US012702561B2

(12) United States Patent
Girouard et al.

(10) Patent No.: US 12,702,561 B2
(45) Date of Patent: Aug. 11, 2026

(54) PATELLA TRIAL IMPLANT

(71) Applicant: Aesculap AG, Tuttlingen (DE)

(72) Inventors: Christophe Girouard, Sarcicourt (FR); Saïd Moussa, Chamarandes-Choignes (FR)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/719,411

(22) PCT Filed: Dec. 14, 2022

(86) PCT No.: PCT/EP2022/085886
§ 371 (c)(1),
(2) Date: Jun. 13, 2024

(87) PCT Pub. No.: WO2023/111034
PCT Pub. Date: Jun. 22, 2023

(65) Prior Publication Data

US 2025/0041068 A1 Feb. 6, 2025

(30) Foreign Application Priority Data

Dec. 15, 2021 (EP) .................................... 21214816

(51) Int. Cl.
*A61F 2/38* (2006.01)
*A61F 2/46* (2006.01)
*A61F 2/30* (2006.01)

(52) U.S. Cl.
CPC .......... *A61F 2/3877* (2013.01); *A61F 2/4684* (2013.01); *A61F 2002/30329* (2013.01)

(58) Field of Classification Search
CPC .................. A61F 2/3877; A61F 2/4684; A61F 2002/30329

(Continued)

(56) References Cited

U.S. PATENT DOCUMENTS 6,146,423 A * 11/2000 Cohen .................. A61F 2/3877 623/20.2
6,602,292 B2 * 8/2003 Burkinshaw .......... A61F 2/3877 623/20.2

(Continued)

FOREIGN PATENT DOCUMENTS

EP 0676182 A1 10/1995
EP 1582184 A1 10/2005

(Continued)

OTHER PUBLICATIONS

Search Report received in International Application No. PCT/EP2022/085886 dated Mar. 31, 2023, 2 pages.

*Primary Examiner* — Jessica Weiss
(74) *Attorney, Agent, or Firm* — Christopher A. Rothe; CM Law

(57) ABSTRACT

A patella trial implant includes: (1) a fixation member having a longitudinal axis extending between a posterior portion and an anterior portion, the anterior portion being configured for fixation to a resected patella, and (2) a patella component having a posterior articular surface configured to articulate with a femoral surface and having an anterior contact surface configured to contact the resected patella and defining a frontal plane of the patella component. The patella component has a guide slot defining at least one guide axis extending longitudinally in parallel to the frontal plane. The posterior portion of the fixation member engages in the guide slot. The patella component and the fixation member are movable relative to each other in translation along the at least one guide axis and in rotation about the longitudinal axis of the fixation member.

20 Claims, 4 Drawing Sheets

(58) Field of Classification Search
USPC ............... 606/88, 96; 623/20.14, 20.18, 20.2
See application file for complete search history.

(56) References Cited

U.S. PATENT DOCUMENTS

| | | | | |
|---|---|---|---|---|
| 6,855,150 | B1 * | 2/2005 | Linehan | A61F 2/461 623/20.18 |
| 7,749,276 | B2 * | 7/2010 | Fitz | A61F 2/46 623/20.18 |
| 2014/0094820 | A1 * | 4/2014 | Clever | A61B 17/1767 606/96 |
| 2014/0148909 | A1 | 5/2014 | Angibaud | |

FOREIGN PATENT DOCUMENTS

| | | | |
|---|---|---|---|
| GB | 2277034 | A | 10/1994 |
| WO | 9742914 | A1 | 11/1997 |

* cited by examiner 6
1
3
7
5
2
F
P
H

1
L
G1
G3
R
P
G2
F

1
G1
G2
F
P
G3

1
P
F

S
1
12
16
18
F
P
17

PATELLA TRIAL IMPLANT

CROSS-REFERENCE TO RELATED APPLICATIONS

This application is the United States national stage entry of International Application No. PCT/EP2022/085886, filed on Dec. 14, 2022, and claims priority to European Application No. 21214816.7, filed on Dec. 15, 2021. The contents of International Application No. PCT/EP2022/085886 and European Application No. 21214816.7 are incorporated by reference herein in their entireties.

FIELD

The present disclosure relates to a patella trial implant for use in total knee arthroplasty (TKA).

BACKGROUND

It is well known that the position of the patella implant in relation to the resected patella has clinical implications for TKA recovery. Typical surgical techniques aim at optimizing the position of the patella implant for both patella-femoral articulation and coverage of the resected patella.

In surgical techniques, the optimal position of the patella implant is assessed by means of a patella trial implant. For this purpose, the patella trial implant is attached temporarily to the resected patella and repositioned iteratively until an optimal position is reached.

US 2014/0148909 A1 discloses a patella trial implant comprising a baseplate and a mobile articular surface member. The baseplate has a medial-lateral axis, a superior-inferior axis and a bottom surface configured to temporarily attach to a resected patella. The mobile articular surface member is in direct physical contact with the baseplate and configured to move translationally along at least one of the medial-lateral axis and the superior-inferior axis of the baseplate.

SUMMARY

One object of the present disclosure is to provide a patella trial implant which allows for a simple and precise repositioning.

According to the present disclosure, a patella trial implant is provided, the patella trial implant comprising: a fixation member having a longitudinal axis extending between a posterior portion and an anterior portion, the anterior portion being configured for fixation to a resected patella; a patella component having a posterior articular surface configured to articulate with a femoral surface and having an anterior contact surface configured to contact the resected patella and defining a frontal plane of the patella component; wherein the patella component has a guide slot defining at least one guide axis extending longitudinally in parallel to the frontal plane, wherein the posterior portion of the fixation member engages in the guide slot, and wherein the patella component and the fixation member are movable relative to each other in translation along the at least one guide axis and in rotation about the longitudinal axis of the fixation member. Hence, the patella trial implant, more specifically the patella component, can be repositioned according to at least one translational degree of freedom (DOF), i.e., along the at least one guide axis, and according to one rotational DOF, i.e., about the longitudinal axis. Providing at least one translational DOF and the rotational DOF allows for a translational and rotational relative mobility between the patella component and the fixation member. In use of the patella trial implant, the orientation of the guide slot, and thus, the at least one guide axis in relation to the resected patella can be changed by rotating the patella component about the longitudinal axis of the fixation member. In other words, the direction of the translational DOF is not static, but can be adjusted very easily and precisely by rotating the patella component about the longitudinal axis of the fixation member. This allows for a very simple and yet precise repositioning of the patella component and its articular surface. The repositioning takes place in relation to the fixation member. In use of the patella trial implant, the fixation member is temporarily attached to the resected patella. Hence, the repositioning takes place in relation to the resected patella. The anterior portion of the fixation member is configured for fixation to the resected patella. In one embodiment, the fixation member is a peg, the anterior portion being configured to fit into a hole prepared in the resected patella. In other embodiments, the fixation member is a screw, the anterior portion comprising a thread for direct fixation to the resected patella. In still other embodiments, the anterior portion has a nail-like shape that allows to nail the fixation member into the resected patella. Suitable adhesives, cement or other bonding materials may help to temporarily fix the anterior portion in the hole and/or the resected patella. The posterior portion of the fixation member is configured to engage in the guide slot of the patella component. In use of the patella trial implant, the posterior portion and the guide slot slidingly interact along the at least one guide axis and about the longitudinal axis. The fixation member extends longitudinally between the posterior and anterior portion. Preferably, the fixation member is elongated in parallel to a posterior-anterior axis of the patella component and/or normal to the frontal plane. In one embodiment, the fixation member has a cylindrical shape. In other embodiments, the fixation member has a rectangular or other geometrical shape. In one embodiment, the patella component is a mono-block component. In other embodiments, the patella component comprises several sub-components, parts, members or the like. The posterior articular surface is configured to articulate with a femoral surface of a prosthesis or a natural femur. The anterior contact surface is configured to temporarily contact the resected patella. The anterior contact surface defines the frontal plane of the patella component. The anterior contact surface is planar, i.e., flat. The anterior contact surface and/or the frontal plane has a medial-lateral axis and a superior-inferior axis. Preferably, the frontal plane and/or the contact surface is normal to the longitudinal axis of the fixation member and/or an anterior-posterior axis. The guide slot defines the at least one guide axis. In one embodiment, the guide axis is parallel to the medial-lateral axis and/or the superior-inferior axis of the frontal plane, i.e., the anterior contact surface. In other embodiments, the at least one guide axis is non-parallel to the medial-lateral axis and/or the superior-inferior axis.

In one embodiment, the at least one guide axis is non-parallel to a medial-lateral axis and to a superior-inferior axis of the frontal plane. Hence, a repositioning along the at least one guide axis results in a simultaneous medial-lateral and superior-inferior repositioning of the patella component with respect to the fixation member. The resulting repositioning mobility has two translational DOF, i.e., a first translational DOF with respect to the medial-lateral axis and a second translational DOF with respect to the superior-inferior axis.

In one embodiment, the guide slot has a plurality of slot sections being interconnected at a juncture and extending longitudinally along different guide axes, along which different guide axes the fixation member and the patella component are movable relative to one another. The slot sections merge at the juncture. The slot sections are elongated at an angle relative to each other. Preferably, the slot sections each extend longitudinally between a first end and a second end, wherein the first ends of the slot sections are connected at and/or merge at the juncture. In use of the patella trial implant, the patella component is movable relative to the fixation member fixed to the resected patella along each of said slot sections, i.e., guide axes. This allows for a further simplified and even more precise repositioning.

In one embodiment, the guide slot has a first slot section extending longitudinally along a first guide axis, a second slot section extending along a second guide axis and a third slot section extending longitudinally along a third guide axis, wherein the first, second and third guide axes are oriented at an angle of 120° relative to each. This allows for a particularly simple and precise translational repositioning. In combination with the rotational DOF about the longitudinal axis of the fixation member, the patella component can be repositioned particularly easily, precisely and quickly within the entire frontal plane.

In one embodiment, the patella component has a round, preferably circular, outer contour comprising a circumferentially extending tooth profile. The tooth profile provides enhanced friction and thus improved grip between the fingers of the surgeon and the outer contour. In use of the patella trial implant, the tooth profile prevents slipping of the fingers on the outer contour. In one embodiment, the tooth profile comprises radial protrusions and/or radial recesses. In one embodiment, the tooth profile is formed by a knurling. In other embodiments, the tooth profile is formed by a serration.

In one embodiment, the articular surface comprises at least one direction marking, preferably an arrow symbol, indicating an orientation of the at least one guide axis of the guide slot. The at least one direction marking provides information to the surgeon for helping to find the optimum translational repositioning of the patella component. The direction marking allows the surgeon to see instantly and easily into which direction the translational repositioning can take place. In case the guide slot comprises a plurality of slot sections defining a plurality of guide axes, the articular surface comprises a plurality of direction markings. In one embodiment, the at least one direction marking is an etch mark. In other embodiments, the at least one direction marking is a laser mark, a lowered mark forming a recess in the articular surface or the like.

In one embodiment, the posterior portion of the fixation member comprises a cylindrical shaft, the cylindrical shaft being guided rotationally and translationally between opposing walls of the guide slot. The guiding formed by the cylindrical shaft and the opposing walls is precise, robust and simple to manufacture. The cylindrical shaft is held between the opposing walls. The cylindrical shaft and the opposing walls are movable relative to each other in translation along the at least one guide axis of the guide slot. The cylindrical shaft and the opposing walls are movable relative to each other in rotation about the longitudinal axis of the fixation member. Preferably, a diameter of the cylindrical shaft is slightly smaller than a width of the guide slot between the opposing walls and/or a normal distance between the opposing walls.

In one embodiment, the posterior portion of the fixation member comprises a radial shoulder, the radial shoulder being positively supported along the longitudinal axis of the fixation member on a web portion of the patella component, preferably of the guide slot. Preferably, the radial shoulder is larger than a minimal width of the guide slot. In use of the patella trial implant, the radial shoulder secures the patella component on the fixation member against a translational movement in anterior-posterior direction and/or along the longitudinal axis of the fixation member. For this purpose, the radial shoulder is positively supported on the web portion. In one embodiment, the web portion protrudes from the opposing walls of the guide slot into the guide slot. Preferably, the web portion protrudes into the guide slot in normal direction of the opposing walls. In case the posterior portion of the fixation member comprises a cylindrical shaft, the radial shoulder is preferably a portion of the cylindrical shaft and/or arranged on the cylindrical shaft. In use of the patella trial implant, the radial shoulder and the web portion are slidably movable relative to each other along the at least one guide axis and about the longitudinal axis of the fixation member.

In one embodiment, the patella component has a locking mechanism which is operatively connected to the posterior portion of the fixation member and/or the guide slot and by means of which locking mechanism relative mobility between the fixation member and the patella component can be locked. In use of the patella trial implant, the locking mechanism allows for a locking of the patella component once a desired position has been reached. The locking mechanism locks the patella component in the desired position in relation to the fixation member, and thus, the resected patella and the femoral surface. The locking mechanism is configured to lock the translational and rotational mobility. The locking mechanism acts on the posterior portion of the fixation member and/or the guide slot. In one embodiment, the locking mechanism is configured to generate friction for locking the relative mobility. In one embodiment, the locking mechanism is configured to generate a form-fit. Said friction and/or form-fit can be generated between the posterior portion of the fixation member and the guide slot. Additionally or as an alternative, said friction and/or form-fit can be generated between a member of the locking mechanism and the posterior portion of the fixation member and/or the guide slot. In a preferred embodiment, relative mobility between the fixation member and the patella component can be locked and unlocked by means of the locking mechanism.

In one embodiment, the locking mechanism comprises a screw member and a friction member, wherein the screw member is adjustable in anterior-posterior direction to press the friction member onto an end face of the posterior portion of the fixation member. For locking and unlocking the relative mobility between the fixation member and the patella component the screw member is adjustable manually or by means of a tool. The screw member acts on the friction member to press the friction member onto the end face of the posterior portion of the fixation member. Pressing the friction member onto the end face increases friction between the friction member and the end face. Increased friction locks the relative mobility between the fixation member and the patella component. Preferably, the screw member acts on the friction member to unpress and/or lift the friction member from the end face of the posterior portion of the fixation member. Unpressing and/or lifting the friction member from the end face decreases friction between the friction member and the end face. Decreased friction unlocks the relative mobility between the fixation member and the patella component. Providing the locking mechanism with the screw member and the friction member allows for a simple and robust locking and unlocking of the relative mobility between the fixation member and the patella component. In one embodiment, the screw member is elongated between a posterior end and an anterior end. The anterior end acts on the friction member. The posterior end is configured for manual actuation and/or actuation by means of a tool. In one embodiment, the friction member has a posterior surface and an opposing anterior surface. The anterior surface is configured to interact with the end face of the posterior portion of the fixation member. The posterior surface is configured to interact with the screw member.

In one embodiment, the patella component comprises at least one drill guide hole extending longitudinally between the anterior contact surface and the posterior articular surface. In use of the patella trial implant, the at least one drill guide hole allows preparation of at least one hole within the resected patella, the at least one hole being configured for the fixation of the final patella implant. Hence, providing the patella component with the at least one drill guide hole allows to prepare the resected patella for the attachment of the final patella implant. This allows for a simplified TKA surgical technique. In conventional surgical techniques, the drill holes for the fixation of the final patella implant are prepared before the assessment of the optimal position which may lead to a wrong positioning and bone loss. Providing the patella component with the at least one drill hole counteracts this disadvantage because the drilling of the holes for the fixation of the final patella implant can be carried out after the repositioning of the patella component, and thus, the assessment of the optimal position.

In one embodiment, the patella component comprises a first drill guide hole, a second drill guide hole and a third drill guide hole, wherein the first, second and third drill guide holes are rotationally offset from each other, preferably by 120°. Providing the patella component with three drill guide holes, i.e., the first, second and third drill guide hole, allows for a simple and quick preparation of three drill holes in the resected patella for the fixation of the final patella implant.

In one embodiment, the patella component has a base plate and a top member mounted onto the base plate, wherein the base plate comprises the contact surface and the guide slot, and wherein the top member comprises the articular surface. Providing the patella component with the base plate and the top member allows for a simple and robust design and an easy manufacturing. In one embodiment, the base plate is manufactured from a metallic material. In one embodiment, the top member is manufactured from a polymeric and/or synthetic material. In one embodiment, the top member is permanently mounted onto the base plate. In other embodiments, the top member is detachably mounted onto the base plate.

In one embodiment, the top member is mounted onto the base plate by means of at least one latching connection. The at least one latching connection can also be referred to as snap-in connection. Preferably, the at least one latching connection is detachable. In other embodiments, the at least one latching connection forms a permanent and/or irremovable connection between the base plate and the top member.

BRIEF DESCRIPTION OF THE DRAWINGS

In the following, an embodiment of the present disclosure will be described in detail with reference to the drawings. Throughout the drawings, the same elements will be denoted by the same reference numerals.

DETAILED DESCRIPTION

Figure 1:
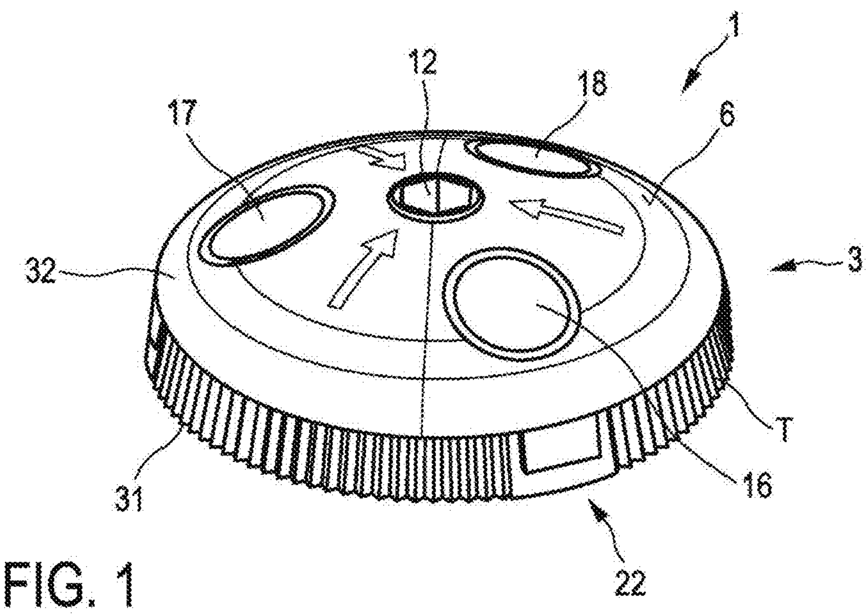
FIG. 1 shows a perspective top view of an embodiment of a patella trial implant according to the present disclosure.
Figure 2:
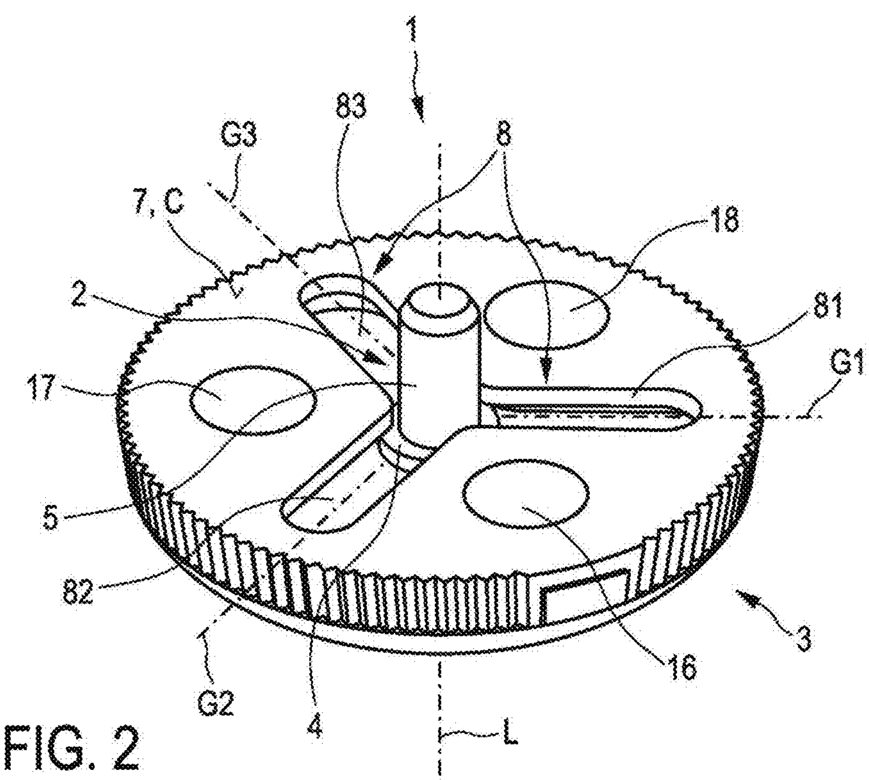
FIG. 2 shows a perspective bottom view of the patella trial implant according to FIG. 1.

According to FIGS. 1 to 4, a patella trial implant 1 comprises a fixation member 2 and a patella component 3. The patella trial implant 1 is intended for use in total knee arthroplasty (TKA).

The fixation member 2 has a longitudinal axis L. The longitudinal axis L extends between a posterior portion 4 and an anterior portion 5. The anterior portion 5 of the fixation member 2 is configured for fixation to a resected patella P.

Figures 5, 6, 7, 8, 9:
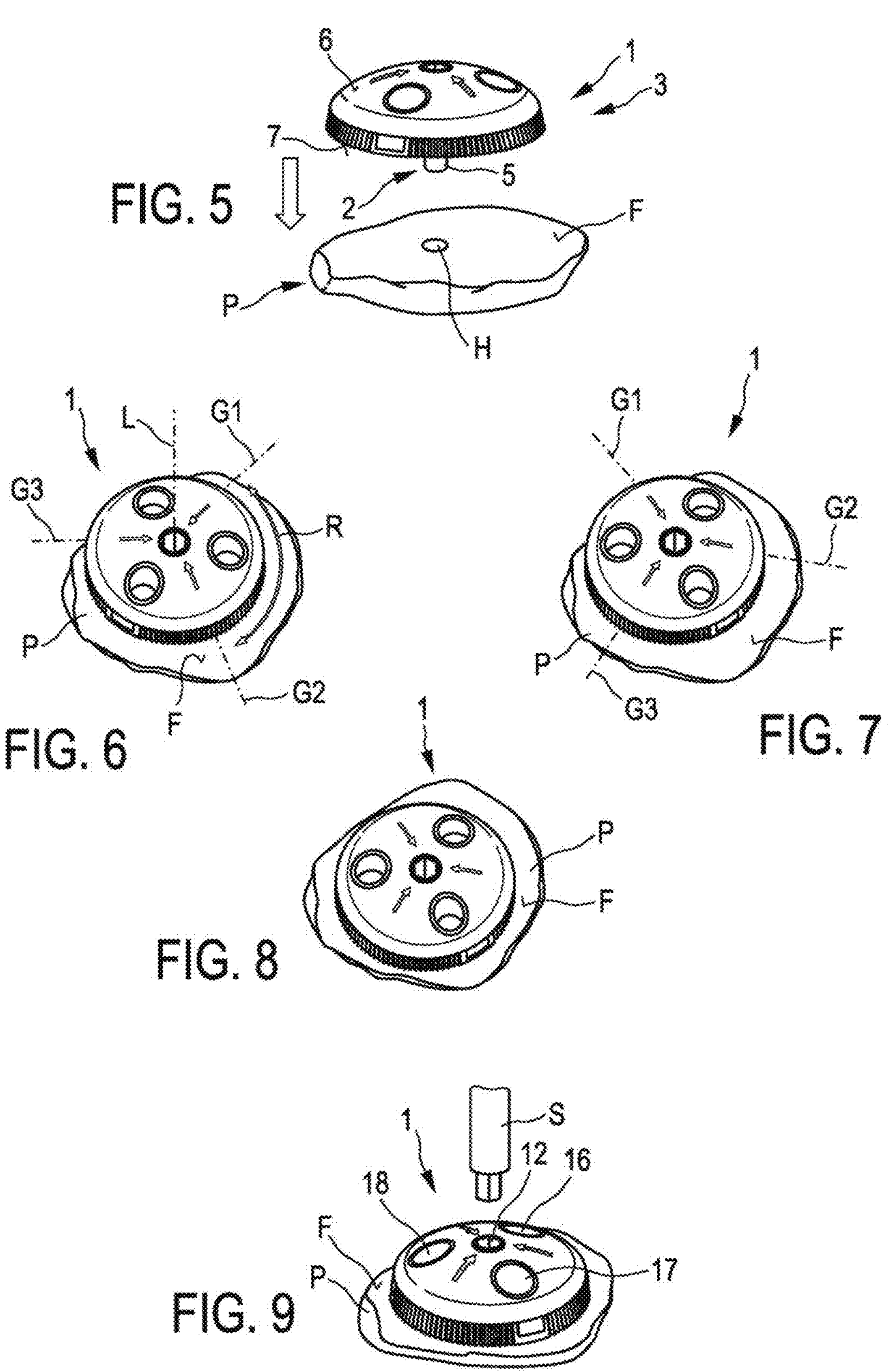
FIGS. 5 to 9 show the patella trial implant according to FIGS. 1 to 4 in different configurations to illustrate the function of the patella trial implant during a total knee arthroplasty.

In the embodiment shown, the anterior portion 5 is configured to fit into a hole H prepared in the resected patella P (see FIG. 5).

In other embodiments not depicted in the figures, the anterior portion comprises a thread or the like for direct fixation to the resected patella. The fixation member can therefore be screwed or nailed to the resected patella without having to drill a hole first. Preparing a hole into the resected patella, as mentioned in connection with the embodiment shown, is therefore not mandatory.

The patella component 3 has a posterior articular surface 6 configured to articulate with a femoral surface. The femoral surface is not shown in the figures and can be a surface of a femoral prosthesis or a surface of a natural femur. Moreover, the patella component 3 has an anterior contact surface 7 configured to contact the resected patella P, more specifically a newly cut posterior surface F of the resected patella (see FIG. 5). The anterior contact surface 7 defines a frontal plane C of the patella component 3.

In the embodiment shown, the posterior articular surface 6 is convex and/or dome-shaped. The anterior contact surface 7 is flat, i.e., planar.

Figure 4:
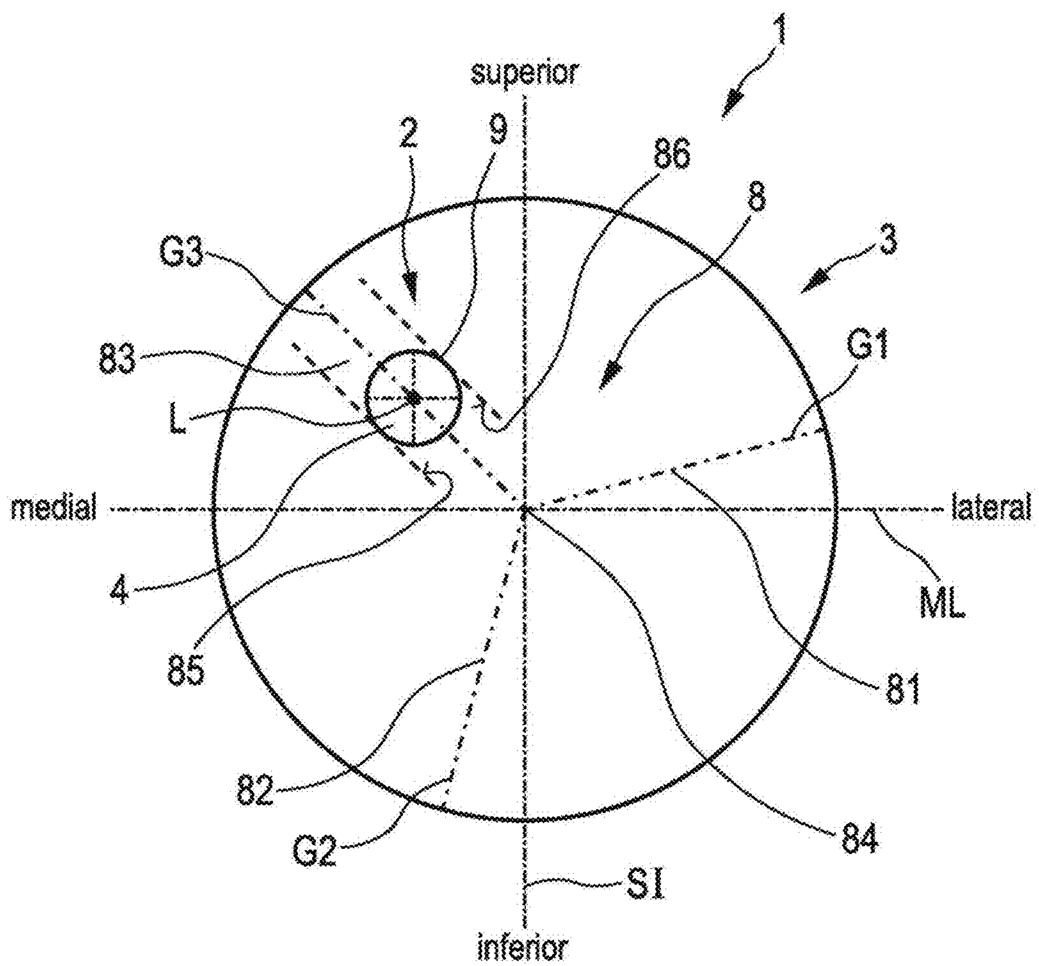
FIG. 4 shows a schematically simplified top view of the patella trial implant according to FIGS. 1 to 3.

As illustrated in FIG. 4, the patella component 3 and/or the frontal plane C defined by the anterior contact surface 7 extend along a medial-lateral axis ML and a superior-inferior axis SI. The longitudinal axis L extends in parallel to an anterior-posterior axis AP of the patella component 3, and thus, in normal direction of the frontal plane C and/or the newly cut surface F of the resected patella P (see FIG. 5).

TKA surgical techniques aim at optimizing the position of the final patella implant for both patella-femoral articulation and coverage of the resected patella. The optimal position of the final patella implant and its posterior articular surface can be assessed by means of the patella trial implant 1. For this purpose, the patella trial implant 1, more specifically its fixation member 2, can be attached temporarily to the resected patella P and the patella component 3 can be repositioned iteratively in relation to the fixation member 2, and thus, the resected patella P until an optimal position is reached.

For the purpose of repositioning, the patella component 3 has a guide slot 8 (see FIGS. 2, 4) defining at least one guide axis G1, G2, G3 extending longitudinally in parallel to the frontal plane C, wherein the posterior portion 4 of the fixation member 2 engages in the guide slot 8, and wherein the patella component 3 and the fixation member 2 are movable relative to each other in translation along the at least one guide axis G1, G2, G3 and in rotation about the longitudinal axis L of the fixation member 2.

As a consequence, the patella trial implant 1, more specifically the patella component 3, can be repositioned according to at least one translational degree of freedom (DOF), i.e., along the at least one guide axis G1, G2, G3, and according to one rotational DOF, i.e., about the longitudinal axis L of the fixation member 2. Providing at least one translational DOF and the rotational DOF allows for a translational and rotational relative mobility between the patella component 3 and the fixation member 2, and hence, the resected patella P. In use of the patella trial implant 1, the orientation of the at least one guide axis G1, G2, G3 can be adjusted in relation to the resected patella P and its newly cut surface F by rotating the patella component 3 about the longitudinal axis L of the fixation member 2. In other words, the direction of the translational DOF for repositioning the patella component 3 is not static, but can be adjusted very easily and precisely by rotating the patella component 3 about the longitudinal axis L. This allows for very simple and yet precise repositioning of the patella component 3 and its posterior articular surface 6.

In the embodiment shown, the guide slot 8 has a plurality of slot sections 81, 82, 83 being interconnected at a juncture 84 (see FIG. 4). The different slot sections 81, 82, 83 extend longitudinally along different guide axes G1, G2, G3. The patella component 3 and the fixation member 2 are movable relative to one another along said different guide axes G1, G2, G3. The slot sections 81, 82, 83 can be referred to as first slot section 81, second slot section 82 and third slot section 83. The according guide axes can be referred to as first guide axis G1, second guide axis G2 and third guide axis G3.

In the embodiment shown, the juncture 84 is located at a center-point and/or midpoint of the patella component 3 with respect to the anterior contact surface 7 and the frontal plane C. In other embodiments, the juncture 84 is spaced from the center point, i.e., off-center or non-central. The different slot sections 81, 82, 83 are interconnected by means of the juncture 84, thereby forming the guide slot 8.

With respect to an imaginary configuration in which the patella component 3 is spatially fixed, the fixation member 2 is movable from one slot section to another by crossing the juncture 84. Starting from the illustrative configuration of FIG. 4, the fixation member 2 is movable within the third slot section 83 along the third guide axis G3 away from and towards the juncture 84. By crossing the juncture 84 the fixation member 2 can be moved into the first slot section G1 and/or the second slot section G2. Of course, in use of the patella trial implant 1, the fixation member 2 is fixed with respect to the resected patella P, and hence, the patella component 3 is therefore movable along said guide axis G1, G2, G3 in relation to the fixation member 2.

Moving the patella component 3 and the fixation member 2 relative to each other translationally along the guide slot and its guide axes G1, G2, G3 allows for a repositioning within the frontal plane C. In order to change the orientation of the guide axes G1, G2, G3 with respect to the medial-lateral axis ML and the superior-inferior axis SI, the patella component 3 can be rotated about the longitudinal axis L. This relative rotation with respect to the fixation member—in use of the patella trial implant 1 with respect to the resected patella P—can take place irrespective of the location of the fixation member 2, more precisely its posterior portion 4, within the guide slot 8.

In the embodiment shown, the first guide axis G1, the second guide axis G2 and the third guide axis G3 are oriented at an angle of 120° relative to each other. As a consequence, the guide slot 8 has a star-like longitudinal extension. The slot sections 81, 82, 83 emanate from and/or merge at the juncture 84.

The posterior portion 4 of the fixation member 2 slidingly engages the guide slot 8. In other words the fixation member 2 and the patella component 3 are slidable relative to each other along the guide axes G1, G2, G3 and about the longitudinal axis L. The posterior portion 4 is in direct physical contact with the guide slot 8.

In the embodiment shown, the posterior portion 4 comprises a cylindrical shaft 9, the cylindrical shaft 9 being guided rotationally and translationally between opposing walls 85, 86 of the guide slot 8 (see FIG. 4). The cylindrical shaft 9 is held between the opposing walls 85, 86. The cylindrical shaft 9 is positively supported within the guide slot 8 in normal direction of the opposing walls 85, 86. In FIG. 4, said opposing walls 85, 86 are schematically illustrated with respect to the third slot section 83. However, it goes without saying that the entire guide slot 8 has opposing walls. In other words, the first slot section 81 and the second slot section 82 each have corresponding opposing walls which are not depicted in great detail in FIG. 4. The cylindrical shaft 9 and the opposing walls 85, 86 slidingly interact along the guide axis and the longitudinal axis L. A diameter of the cylindrical shaft 9 is slightly smaller than a width of the guide slot 8 between the opposing walls and/or a normal distance between the opposing walls.

Figure 3:
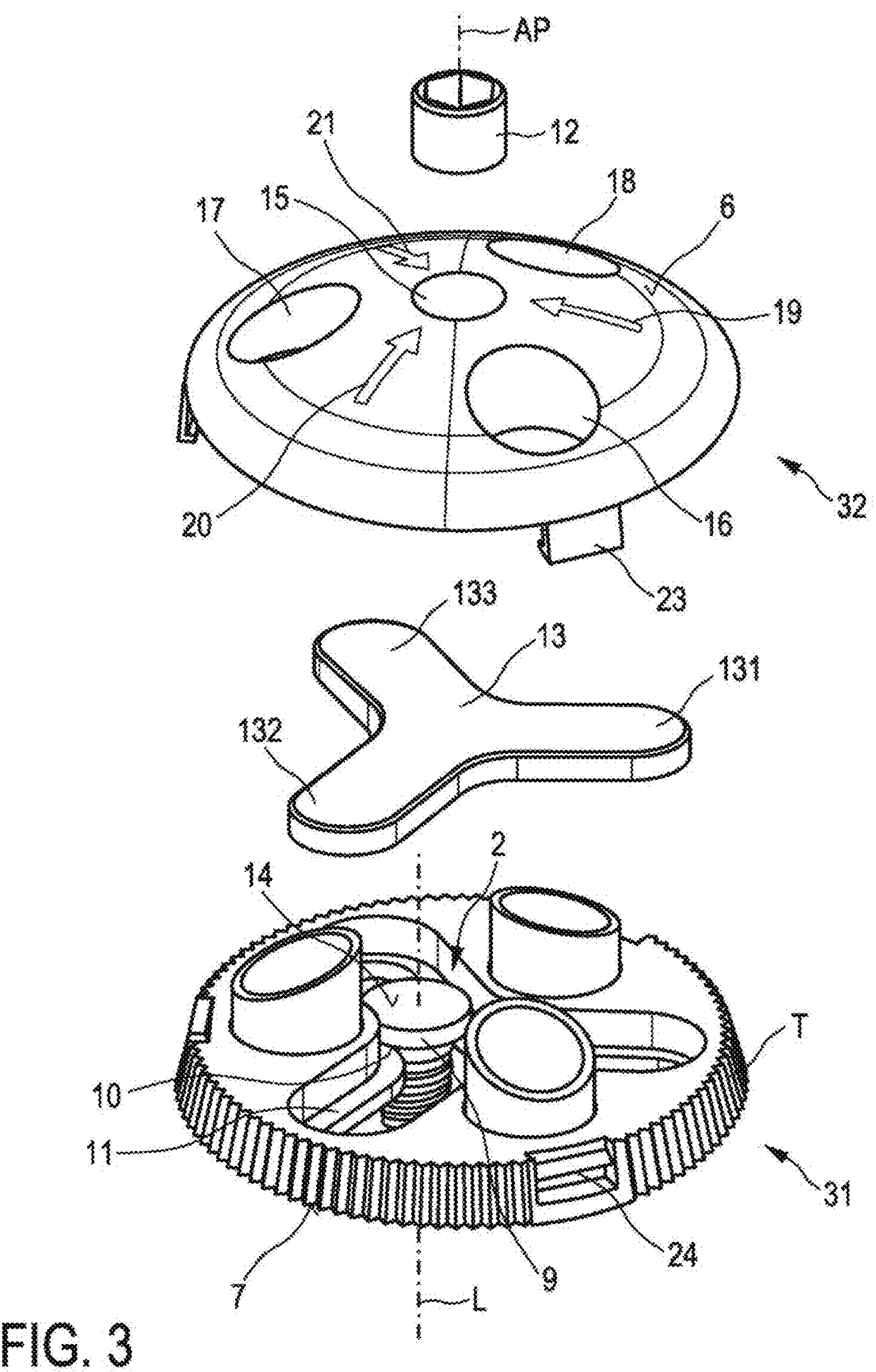
FIG. 3 shows an exploded perspective view of the patella trial implant according to FIGS. 1 and 2.

In the embodiment shown, the posterior portion 4 comprises a radial shoulder 10, the radial shoulder being positively supported along the longitudinal axis L on a web portion 11 of the patella component 3 (see FIG. 3). In the embodiment shown, the radial shoulder 10 is formed by an anterior end face of the cylindrical shaft 9. The radial shoulder 10 contacts the web portion 11 in anterior direction. The radial shoulder 10 and the web portion 11 slidingly interact with each other translationally along the guide axes of the guide slot 8 and rotationally about the longitudinal axis L. The web portion 11 protrudes from the opposing walls 85, 86 in normal direction, i.e., into the guide slot 8. The web portion 11 extends circumferentially along the entire guide slot 8.

In the embodiment shown, the patella component 3 comprises a locking mechanism 12, 13 which is operatively connected to the posterior portion 4 of the fixation member 2 and/or the guide slot 8 and by means of which locking mechanism 12, 13 relative mobility between the fixation member 2 and the patella component 3 can be locked (see FIG. 3). The locking mechanism 12, 13 allows locking the patella component 3 in relation to the fixation member 2 once a desired position has been reached. The locking mechanism 12, 13 is configured to lock the translational and rotational mobility of the patella component 3 in relation to the fixation member 2. The locking mechanism 12, 13 is configured to generate friction for locking the relative mobility. In other embodiments, the locking mechanism is configured to generate a form fit between the fixation member and the guide slot.

In the embodiment shown, the locking mechanism 12, 13 comprises a screw member 12 and a friction member 13. The screw member 12 is adjustable in anterior-posterior direction, i.e., along the anterior-posterior axis AP of the patella component (see FIG. 3). Adjusting the screw member 12 along the anterior-posterior axis AP allows pressing the friction member 13 onto an end face 14 of the posterior portion 4. The screw member 12 has an outer thread which is not depicted in great detail and which interacts with an inner thread of the patella component 3. The inner thread is located within a threaded hole 15 of the patella component 3. The threaded hole 15 is oriented coaxially with respect to the anterior-posterior axis AP. Moreover, the threaded hole 15 is located centrally with respect to the posterior articular surface 6 and/or the anterior contact surface 7. Furthermore, the threaded hole 15, and thus, the screw member 12 is located directly above the juncture 84.

The friction member 13 has a plate-like form and covers the guide slot 8 in posterior direction. Adjusting the screw member 12 in anterior direction presses the friction member 13 onto the end face 14. This generates increased friction and thereby a locking of the relative position between the patella component 3 and the fixation member 2. Since the friction member 13 covers the entire guide slot 8, said locking can take place irrespective of the relative position of the fixation member 2 within the guide slot 8.

In the embodiment shown, the friction member 13 comprises a first arm 131, a second arm 132 and a third arm 133. The first arm 131 covers the first slot section 81. The second arm 132 covers the second guide slot 82. The third arm 133 covers the third guide slot 83. A central section of the friction member 13 covers the juncture 84.

In the embodiment shown, the fixation member 13 is held between the opposing walls 85, 86 of the guide slot.

Adjusting the screw member 12 in anterior direction unpresses the friction member 13 from the end face 14. This reduces the friction between the friction member 13 and the end face 14 and releases and/or unlocks the relative mobility between the fixation member 2 and the patella component 3.

In the embodiment shown, the patella component 3 comprises a first drill guide hole 16, a second drill guide hole 17 and a third drill guide hole 18. In other embodiments, the patella component 3 comprises one, two or more than three drill guide holes.

The drill guide holes 16, 17, 18 each extend longitudinally between the anterior contact surface 7 and the posterior articular surface 6. The longitudinal axes of the drill guide holes 16, 17, 18 extend in parallel to the anterior-posterior axis AP. The drill guide holes 16, 17, 18 each are configured to guide a drilling tool for the preparation of the newly cut surface F of the resected patella P. The bore holes prepared with said drilling tool are intended for the fixation of the (final) patella implant, once the optimal position has been assessed by repositioning the patella trial implant 1.

In the embodiment shown, the first, second and third drill guide holes 16, 17, 18 are rotationally offset from each other by 120° around the anterior-posterior axis AP.

The first drill guide hole 16 is located between the first slot section 81 and the second slot section 82 (see FIGS. 3, 4). The second drill guide hole 17 is located between the second slot section 82 and the third slot section 83. The third drill guide hole 18 is located between the third slot section 83 and the first slot section 81.

In the embodiment shown, the articular surface 6 comprises a plurality of direction markings 19, 20, 21 indicating an orientation of the different guide axes G1, G2, G3. The direction markings 19, 20, 21 can be denoted as first direction marking 19, second direction marking 20 and third direction marking 21. The first direction marking 19 indicates the orientation of the first guide axis G1. The second direction marking 20 indicates the orientation of the second guide axis G2. The third direction marking 21 indicates the orientation of the third guide axis G3. In the embodiment shown, the direction markings 19, 20, 21 each are in the form of an arrow symbol. The direction markings 19, 20, 21 are printed on the articular surface 6. In other embodiments, the direction markings are etch marks, lowered marks or the like.

In the embodiment shown, the patella component 3 has a base plate 31 and a top member 32.

The base plate 31 comprises the anterior contact surface 7 and the guide slot 8 (see FIG. 3). The base plate 31 has a round, more specifically circular, outer contour comprising a circumferentially extending tooth profile T. The tooth profile T generates increased friction between the fingers of the surgeon and the outer contour. This allows for an improved grip of the fingers on the patella component 3, and thus, a more safe and precise repositioning.

The base plate 31 is manufactured from a metallic material. In other embodiments, a polymeric or synthetic material is used for the base plate 31. In the embodiment shown, the top member 32 is manufactured from a polymeric or synthetic material.

The top member 32 is mounted onto the base plate 31 and comprises the articular surface 6. Moreover, the top member 32 comprises the threaded hole 15.

In the embodiment shown, the top member 32 is mounted onto the base plate 31 by means of a plurality of latching connections, wherein within the figures one latching connection 22 is depicted in greater detail. The latching connection 22 is formed between a latch member 23 and a notch member 24 (see FIGS. 1, 3). The top member 32 comprises the latch member 23. The base plate 31 comprises the notch member 24.

In the embodiment shown, the latching connection 22 is configured to irremovably attach the top member 32 onto the base plate 31. In other embodiments, the latching connection is configured for removably attaching the top member onto the base plate.

The drill guide holes 16, 17, 18 extend through the top member 32 and the base plate 31. The friction member 13 is held between the base plate 31 and the top member 32 along the anterior-posterior axis AP.

In other embodiments, the patella component 3 features a mono-block design, i.e., is designed as a monolithic part.

FIGS. 5 to 9 illustrate the function of the patella trial implant 1 during a TKA surgical procedure.

In a first step, the patella trial implant 1 is placed on the resected patella P (FIG. 5). The resected patella P comprises the newly cut surface F and, in the embodiment shown, the hole H, wherein the hole H is prepared at a peak point of the resected patella P. For temporarily attaching the patella trial implant 1 to the resected patella P, the fixation member 2, more specifically its anterior portion 5, is fitted into the hole H. Once placed onto the resected patella P, the anterior contact surface 7 slidingly contacts the newly cut surface F.

In an embodiment not shown in the figures, the fixation member is screwed to the resected patella without the need to first drill a hole. In still another embodiment, it is envisioned to nail the fixation member directly to resected patella.

In a second step (FIG. 6), the patella component 3 and its posterior articular surface 6 are repositioned by rotation with respect to the fixation member 2, and thus, the resected patella. Said rotational repositioning is indicated in FIG. 6 by means of an arrow symbol R. The rotational repositioning takes place about the longitudinal axis L of the fixation member 2. In the configuration shown in FIG. 6, the guide axes G1, G2, G3 have a certain orientation with respect to the planar surface C, i.e. the medial-lateral axis ML, and the superior-inferior axis SI of the frontal plane C, and thus, the newly cut surface F. The rotational repositioning changes the orientation of the guide axes G1, G2, G3.

FIG. 7 illustrates the situation after the rotational repositioning. Hence, the orientations of the guide axes G1, G2, G3 have changed. Starting from the configuration illustrated in FIG. 7, the patella component 3 is translationally repositioned along the first guide axis G1. FIG. 8 illustrates the situation after the translational repositioning.

FIGS. 6 to 8 illustrate that the patella component 3 can be repositioned easily and precisely until a desired and/or needed position is found in relation to the resected patella and/or the femoral surface.

Once an optimal position is found, relative mobility of the patella component 3 in relation to the fixation member 2 and the resected patella P can be locked by actuating the locking mechanism 12, 13, i.e., by adjusting the screw member 12 in anterior direction. For adjusting the screw member, a dedicated tool S can be used. After locking the patella component 3 in place, the preparation of the resected patella P for the attachment of the final patella implant can take place by drilling holes with the help of the drill guide holes 16, 17, 18.

One main advantage of the patella trial implant 1 is that the preparation of the resected patella P for the attachment of the final patella implant can take place after assessing the optimal position.

The invention claimed is:

1. A patella trial implant comprising:

a fixation member having a longitudinal axis extending between a posterior portion and an anterior portion, the anterior portion being configured for fixation to a resected patella; and a patella component having a posterior articular surface configured to articulate with a femoral surface and having an anterior contact surface configured to contact the resected patella and defining a frontal plane of the patella component, the patella component comprising a guide slot defining at least one guide axis extending longitudinally in parallel to the frontal plane, wherein the posterior portion of the fixation member engages in the guide slot, and wherein the patella component and the fixation member are movable relative to each other in translation along the at least one guide axis and in rotation about the longitudinal axis of the fixation member.

2. The patella trial implant according to claim 1, wherein the at least one guide axis is non-parallel to a medial-lateral axis and to a superior-inferior axis of the frontal plane.

3. The patella trial implant according to claim 1, wherein the guide slot has a plurality of slot sections being interconnected at a juncture and extending longitudinally along different guide axes, along which different guide axes the fixation member and the patella component are movable relative to one another.

4. The patella trial implant according to claim 3, wherein the plurality of slot sections comprise a first slot section extending longitudinally along a first guide axis, a second slot section extending longitudinally along a second guide axis, and a third slot section extending longitudinally along a third guide axis, wherein the first guide axis, the second guide axis, and the third guide axis are oriented at an angle of 120° relative to each.

5. The patella trial implant according to claim 1, wherein the patella component has a round outer contour comprising a circumferentially extending tooth profile.

6. The patella trial implant according to claim 1, wherein the posterior articular surface comprises at least one direction marking located adjacent to the guide slot along the longitudinal axis and extending along the at least one guide axis thereby indicating an orientation of the at least one guide axis of the guide slot.

7. The patella trial implant according claim 1, wherein the posterior portion of the fixation member comprises a cylindrical shaft, the cylindrical shaft being guided rotationally and translationally between opposing walls of the guide slot.

8. The patella trial implant according to claim 1, wherein the posterior portion of the fixation member comprises a radial shoulder, the radial shoulder being positively supported along the longitudinal axis of the fixation member on a web portion of the patella component.

9. The patella trial implant according to claim 1, wherein the patella component has a locking mechanism which is operatively connected to the posterior portion of the fixation member and/or the guide slot and by means of which locking mechanism relative mobility between the fixation member and the patella component can be locked.

10. The patella trial implant according to claim 9, wherein the locking mechanism comprises a screw member and a friction member, wherein the screw member is adjustable in an anterior-posterior direction to press the friction member onto an end face of the posterior portion of the fixation member.

11. The patella trial implant according to claim 1, wherein the patella component comprises at least one drill guide hole extending longitudinally through the anterior contact surface and the posterior articular surface.

12. The patella trial implant according to claim 11, wherein the at least one drill guide hole comprises a first drill guide hole, a second drill guide hole and a third drill guide hole, wherein the first drill guide hole, the second drill guide hole and the third drill guide hole are rotationally offset from each other.

13. The patella trial implant according to claim 1, wherein the patella component has a base plate and a top member mounted onto the base plate, wherein the base plate comprises the anterior contact surface and the guide slot, and wherein the top member comprises the posterior articular surface.

14. The patella trial implant according to claim 13, wherein the top member is mounted onto the base plate by at least one latching connection.

15. A patella trial implant comprising:

a fixation member having a longitudinal axis extending between a posterior portion and an anterior portion, the anterior portion being configured for fixation to a resected patella; and a patella component having a posterior articular surface configured to articulate with a femoral surface and having an anterior contact surface configured to contact the resected patella and defining a frontal plane of the patella component, the patella component comprising a guide slot defining at least one guide axis extending longitudinally in parallel to the frontal plane, wherein the posterior portion of the fixation member engages in the guide slot, and wherein the patella component and the fixation member are movable relative to each other in translation along the at least one guide axis and in rotation about the longitudinal axis of the fixation member, wherein the guide slot has a plurality of slot sections being interconnected at a juncture and extending longitudinally along different guide axes, along which different guide axes the fixation member and the patella component are movable relative to one another.

16. The patella trial implant according to claim 15, wherein the guide slot has a first slot section extending longitudinally along a first guide axis, a second slot section extending longitudinally along a second guide axis, and a third slot section extending longitudinally along a third guide axis, wherein the first guide axis, the second guide axis, and the third guide axis are oriented at an angle of 120° relative to each.

17. A patella trial implant comprising:

a fixation member having a longitudinal axis extending between a posterior portion and an anterior portion, the anterior portion being configured for fixation to a resected patella; and a patella component having a posterior articular surface configured to articulate with a femoral surface and having an anterior contact surface configured to contact the resected patella and defining a frontal plane of the patella component, the patella component comprising a guide slot defining at least one guide axis extending longitudinally in parallel to the frontal plane, wherein the posterior portion of the fixation member engages in the guide slot, and wherein the patella component and the fixation member are movable relative to each other in translation along the at least one guide axis and in rotation about the longitudinal axis of the fixation member, wherein the patella component has a locking mechanism which is operatively connected to the posterior portion of the fixation member and/or the guide slot and by means of which locking mechanism relative mobility between the fixation member and the patella component can be locked.

18. The patella trial implant according to claim 17, wherein the locking mechanism comprises a screw member and a friction member, wherein the screw member is adjustable in an anterior-posterior direction to press the friction member onto an end face of the posterior portion of the fixation member.

19. A patella trial implant comprising:

a fixation member having a longitudinal axis extending between a posterior portion and an anterior portion, the anterior portion being configured for fixation to a resected patella; and a patella component having a posterior articular surface configured to articulate with a femoral surface and having an anterior contact surface configured to contact the resected patella and defining a frontal plane of the patella component, the patella component comprising a guide slot defining at least one guide axis extending longitudinally in parallel to the frontal plane, wherein the posterior portion of the fixation member engages in the guide slot, and wherein the patella component and the fixation member are movable relative to each other in translation along the at least one guide axis and in rotation about the longitudinal axis of the fixation member, wherein the patella component has a base plate and a top member mounted onto the base plate, wherein the base plate comprises the anterior contact surface and the guide slot, and wherein the top member comprises the posterior articular surface.

20. The patella trial implant according to claim 19, wherein the top member is mounted onto the base plate by at least one latching connection.

* * * * *